(12) United States Patent
Pettit et al.

(10) Patent No.: US 6,777,578 B2
(45) Date of Patent: Aug. 17, 2004

(54) HYDROXYPHENSTATIN AND THE PRODRUGS THEREOF

(75) Inventors: George R. Pettit, Paradise Valley, AZ (US); Matthew P. Grealish, San Diego, CA (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 10/258,676

(22) PCT Filed: Apr. 27, 2001

(86) PCT No.: PCT/US01/13731

§ 371 (c)(1),
(2), (4) Date: Apr. 24, 2003

(87) PCT Pub. No.: WO01/81288

PCT Pub. Date: Nov. 1, 2001

(65) Prior Publication Data

US 2003/0220304 A1 Nov. 27, 2003

Related U.S. Application Data

(60) Provisional application No. 60/200,394, filed on Apr. 27, 2000.

(51) Int. Cl.[7] .......................... C07C 49/76; A01N 35/00
(52) U.S. Cl. ....................... 568/332; 568/333; 514/686; 514/687
(58) Field of Search ................................ 568/332, 333; 514/686, 687

(56) References Cited

U.S. PATENT DOCUMENTS 4,145,444 A  3/1979  Hamazaki et al.
5,561,122 A  10/1996  Pettit
5,886,025 A  3/1999  Pinney

OTHER PUBLICATIONS

Pettit et al. Antineoplastic Agents. 379. Synthesis of Phenstatin Phosphate.□□J. Medicinal Chemistry, 1998, vol. 41, p 1688–1695.*

Pettit et al. Antineoplastic Agents. 443. Synthesis of the Cancer Cell Growth Inhibitor Hydroxyphenstatin and its Sodium Diphosphate Drup.□□J. Medicinal Chemistry, 2000, vol. 43, p 2731–2737.*

Pettit et al. A Pinacol Rearrangement/Oxidation Synthetic Route to Hydroxyphenstatin.□□J. Organic Chemistry, 2000, vol. 65, p 7438–7444.*

* cited by examiner

Primary Examiner—Shailendra Kumar
Assistant Examiner—Sikarl A. Witherspoon
(74) Attorney, Agent, or Firm—Fennemore Craig, P.C.; Richard Mybeck

(57) ABSTRACT

The benzophenone derivative of combretastatin A-1, designated "hydroxyphenstatin", was synthesized by compiling a protected bromobenzene and a benzaldehyde to form a benzhydrol which was subsequently oxidized to the ketone. Hydroxyphenstatin was converted to a sodium phosphate prodrug by dibenzyl phosphite phosphorylation and subsequent benzyl cleavage: Hydroxyphenstatin and the prodrugs thereof were found to be a potent inhibitor of tubulin polymerization and to demonstrate surprisingly effective antineoplastic activity against a series of human cancer cells and murine P388 lymphocytic leukemia cells.

4 Claims, 1 Drawing Sheet

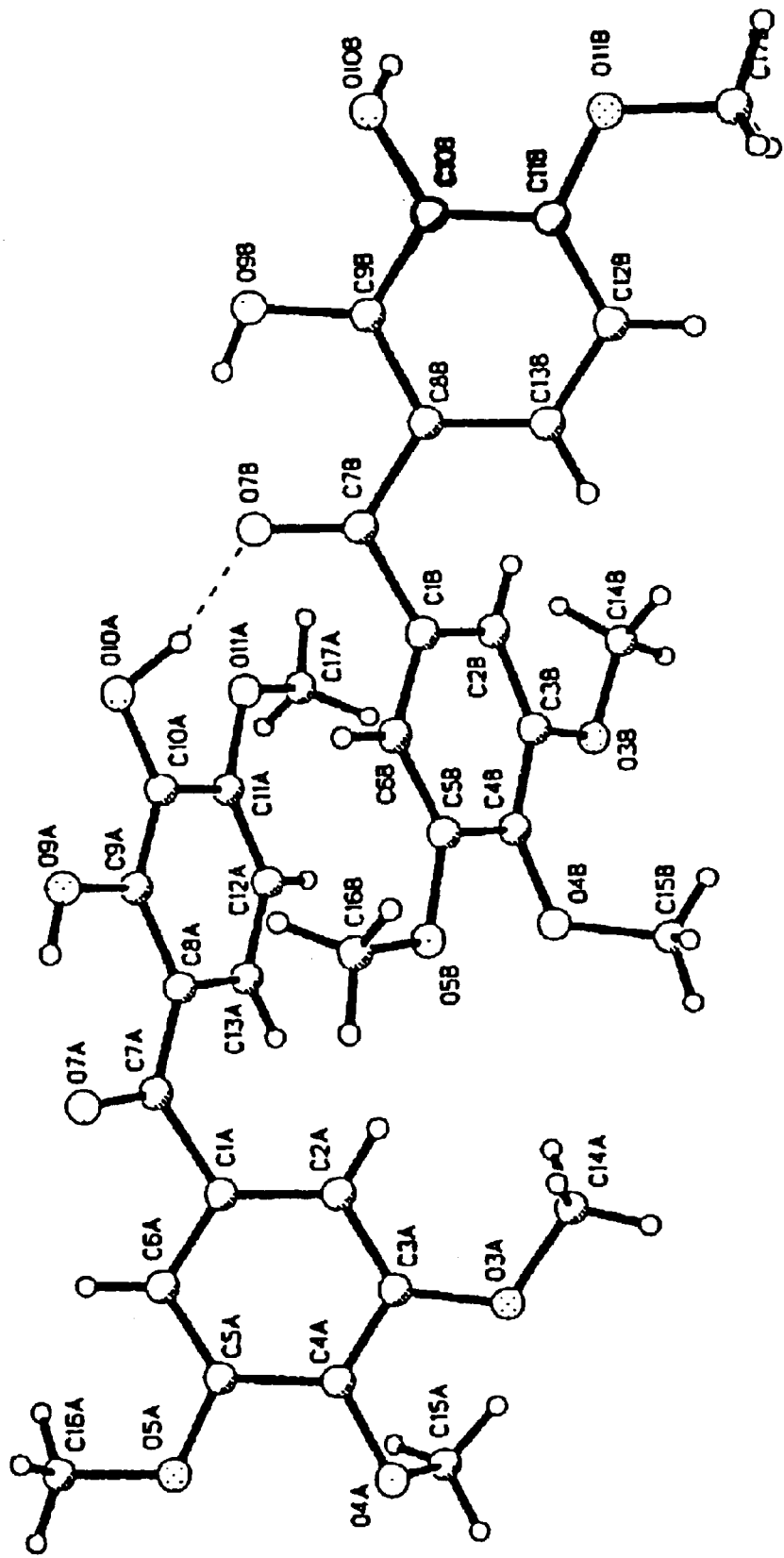

HYDROXYPHENSTATIN AND THE PRODRUGS THEREOF

This application is a U.S. national stage PCT application of PCT/US01/13731 filed on Apr. 27, 2001, which claims the priority of U.S. provisional application Serial No. 60/200,394 filed on Apr. 27, 2000.

This research was funded in part by Outstanding Investigator Grant CA44344-01-11 awarded by the Division of Cancer Treatment, National Cancer Institute, DHHS. The United States government may have certain rights to this invention.

INTRODUCTION

The present invention relates generally to the field of chemotherapy and more particularly to the invention of novel anti-neoplastic agents denominated "hydroxyphenstatin" and selected prodrugs thereof.

BACKGROUND OF THE INVENTION

The elucidation and isolation of agents from the African bush willow *combretum caffrum* first identified combretastatin A-4 as described in U.S. Pat. No. 4,996,237 which issued to G. R. Pettit et al., on Feb. 26, 1991. Other early efforts to develop a combretastatin A-4 prodrug are described in U.S. Pat. No. 5,561,122, which issued to G. R. Pettit on Oct. 1, 1996. The general background information from each of these patents is incorporated herein by this reference thereto.

The potent cancer cell growth and tubulin assembly inhibitor combretastatin A-4 was originally isolated from the African tree *Combretum caffrum* (Combretaceae) circa 1985 and has been undergoing preclinical development since that time. However, because of the very limited aqueous solubility of the phenol and its alkali metal salts, drug formulation attempts gave unsatisfactory results. Accordingly, the present disclosure comprises a benchmark in the continuing effort to synthesize practical water soluble prodrugs based on combretastatin A-4 and is a significant and remarkably unexpected extension of those early efforts which are described in U.S. Pat. No. 5,561,122, supra.

The African willow tree *Combretum caffrum* Kuntze (Combretaceae) has proven to be a very productive source of cancer cell growth (murine P388 lymphocytic leukemia) inhibitory stilbenes, bibenzyls and phenanthrenes. Since 1979 promising leads have been pursued which were focused on the three most active (inhibition of cancer cell growth and polymerization of tubulin (Id.)) constituents, namely combretastatin A-1 (3a), A-2 (4), and A-4 (3b) (Id.) (See, FIG. 1). Of these, combretastatin A-4 (3b) has reached the most advanced stage of preclinical development as the very soluble prodrug 3c. Meanwhile other research groups have also been further extending structure/activity relationships (hereinafter referred to as "SAR") among the combretastatins and related stilbenes.

The formation of new blood vessels, known as "angiogenesis" (neovascularisation), is controlled by a very complex series of biochemical interactions involving a large number of angiogenic factors ranging from various cytokines (e.g. IL-1) and growth factors (e.g., GM-CSF) to serine proteases (e.g. urokinase). In general, normal angiogenesis involves the activation and transport of endothelial cells from already formed blood vessels to new locations. Normally that transition takes three (3) months to a year except in wound healing and in certain stages of female reproductive biology. When the angiogenic control mechanisms fail, the results lead to a wide range of human disease categories, such as cancer, psoriasis, hemangioma, atherosclerotic plaque, diabetic and macular retinopathy, neovascular glaucoma, and vascular adhesions following surgery.

Because the African bush willow (*Combretum caffrum*) constituents, (Isolation, Structure and Synthesis of Combretastatin A-1 and Combretastatin B-1, Potent New Inhibitors of Microtubule Assembly, Derived from *Combretum caffrum. J. Nat. Prod.* 1987, 50, 119–131), combretastatins A-1 (3a) and A-4 (3b) were isolated and designated as well as their phosphate prodrug; (Pettit, G. R.; Rhodes, M. R. Antineoplastic Agents 389. New Syntheses of Combretastatin A-4 Prodrug. *Anti-Cancer Drug Des.* 1998, 13, 183–191; and Pettit, G. R.; Lippert, J. W. III. Antineoplastic Agents 429. Synthesis of Combretastatin A-1 and Combretastatin B-1 Prodrugs. *Anti-Cancer Drug Des.* 1999, in preparation.), derivatives (3c,e) which displayed very promising antineoplastic, cancer antiangiogenesis. Recently extended SAR investigations of these cis-stilbenes have been conducted. Indeed, combretastatin A-4 prodrug (3c) has been undergoing a series of phase I human cancer clinical trials since November 1998.

Previous SAR analyses of the combretastatin A-4 series have indicated that the cis configuration of the stilbene unit is the most important factor for inhibition of cancer cell growth and inhibiting tubulin assembly. With the corresponding (E)-stilbenes, the cancer cell growth inhibitory and antitubulin activity is greatly reduced from that exhibited by the corresponding (Z)-isomers. Initially, both the trans-isomers and were found to be moderately active as cancer cell growth inhibitors. Later studies using trans-stilbene revealed that freshly prepared solutions in dimethyl sulfoxide were inactive and only gained activity with the passage of time suggesting that the trans-isomers were slowly converted to the cis active isomer.

Furthermore, a structure-activity relationship (SAR) study of the South African willow tree (*Combretum caffrum*) antineoplastic constituent combretastatin A-4 (3b) led to the discovery of a potent cancer cell growth inhibitor designated phenstatin (5a). This benzophenone derivative of combretastatin A-4 showed great antineoplastic activity and the benzophenone derivative of combretastatin A-1 was synthesized. The benzophenone, designated hydroxyphenstatin (6a), was synthesized by coupling of a protected bromobenzene and a benzaldehyde to give the benzhydrol with subsequent oxidation to the ketone. Hydroxyphenstatin was converted to the sodium phosphate prodrug (6e) by a dibenzyl phosphite phosphorylation and subsequent benzyl cleavage (6a→6d→6e). Hydroxyphenstatin (6a) was a potent inhibitor of tubulin polymerization comparable to combretastatin A-1 (3a).

Podophyllum, the roots and rhizomes of Podophyllum species such as *Peltatumi L.* (Podophyllaceae, May Apple) found important uses including cancer and antiviral applications in the traditional medicine of early Americans and in India. Indeed, it was an important component of the U.S. Pharmacopoeia from 1820–1942 (the derived resin has been found to contain up to 38% podophyllotoxin (1a) and was the first terrestrial plant anticancer agent developed to clinical trials by the U.S. National Cancer Institute some fifty years ago. Subsequently, podophyllotoxin has been converted to the glycoside derivative known as etoposide (1b), now widely used in human cancer treatment.

In 1958, a SAR investigation was initiated which focused on the trimethoxy and methylenedioxy diarylmethylene unit of podophyllotoxin (1a). While not detected at the time, owing to limitations of the early antineoplastic evaluation options, it was later found that the diarylketone (2) significantly inhibited the growth of the P388 lymphocytic leukemia cell line with an $ED_{50}$ value of 2.6 µg/ml. By 1978, while investigating the cancer cell growth inhibition of the African willow tree *Combretum caffrum* Kuntze (Combretaceae) three potentially important constituents were discovered which were designated combretastatins A-1 (3a), A-2 (4), and A-4 (3b). Combretastatin A-4, as the water soluble prodrug (3c), subsequently reached the most advanced stage of preclinical and clinical development. More recently, the diarylketone named phenstatin (5a) was discovered (See: Pettit, G. R.; Toki, B.; Herald, D. L.; Verdier-Pinard, P.; Boyd, M. R.; Hamel, E.; Pettit, R. K. Antineoplastic Agents 379. Synthesis of Phenstatin Phosphate. *J. Med Chem.* 1998, 41, 1688–1695) which was found to be structurally related to podophyllotoxin (1a) and combretastatin A-4 (3b) and proved to be a very strong anticancer substance comparable to stilbene (3b). These and other results (See: Pettit, G. R.; Lippert, J. W. III; Boyd, M. R.; Hamel, E.; Pettit, R. K. Antineoplastic Agents 442. The Remarkable Antitubulin Assembly and Cancer Cell Growth Inhibition of (4S,5S)-4-(2",3"-dihydroxy-4"-methoxyphenyl)-5-(3',4',5'-trimethoxyphenyl)-1,3-dioxolane. *J. Med Chem.* in preparation) encouraged efforts to undertake the synthesis and evaluation of diphenol (6a).

The general procedure reported in 1962 for obtaining ketone (2) (See: Pettit, G. R.; Baumann, M. F.; Rangammal, K. N. Antineoplastic Agents V. The Aromatic System of Podophyllotoxin (Part B). *J. Med Pharm.* 1962, 5, 800–808) was attempted first. Coupling reactions between 2,3-bis(t-butyldimethylsilyloxy)-4-methoxy-bromobenzene (7b) and N-(3,4,5-trimethoxybenzoyl)morpholine (8a) utilizing either n-butyl- or tert-butyllithium were unsuccessful. Changing the acylating agent to a benzoyl chloride was also not productive. Presumably, the bulky TBDMS substituents caused enough steric hindrance to prevent nucleophilic attack of the lithium-benzene complex on the carbonyl group. Thus, the smaller methoxymethyl ether (MOM) protecting group was next chosen. (See: Greene, T. W.; Wutz, P. G. M. *Protective Groups in Organic Synthesis.* J. Wiley & Sons: New York, 1999; pp. 27–33). However, formation of the benzophenone using the MOM-protected bromobenzene (7c) and either the morpholine amide (8a) or the benzoyl chloride (8b) met only with limited success, affording 24% and 20% yields, respectively. Further attempts to prepare protected diphenol (6c) using Grignard reactions, Weinreb amides, (See: Nahm, S.; Weinreb, S. M. N-Methoxy-N-methylamides as Effective Acylating Agents. *Tetrahedron Lett.* 1981, 22, 3815–3818), and dimethylamides also afforded low yields (14–44%). Application of organometallic reagents such as $La(OTf)_3$, $Bu_3P$ and $Fe(acac)_3$ did not provide improved yields of ketone (6c).

In order to determine if the protecting groups were interfering, ketone formation was evaluated starting with 2,3,4-trimethoxybromobenzene (9) and morpholine amide (8a). The resulting yields were found to range from 17–20%. These results indicated that the protecting groups used in the preceding reaction may not have significantly influenced the poor yields. Later, however, it was found that condensing the bromobenzene (9) with 3,4,5-trimethoxybenzaldehyde led to the formation of benzhydrol (14) in 86% yield. Subsequent oxidation with pyridinium dichromate (PDC) to benzophenone (13) provided 83% yield. These favorable results led to the utilization of the efficient reaction between an aldehyde and an organolithium reagent to prepare a benzhydrol derivative of ketone (6a). This approach was realized when the lithium derivative of MOM-protected bromobenzene (7c) and 3,4,5-trimethoxybenzaldehyde were condensed to afford protected benzhydrol (15) in 92% yield. Oxidation of protected benzhydrol by PDC produced protected hydroxyphenstatin (6c) in good yield (96%) and MOM-cleavage (acidic) afforded hydroxyphenstatin (6a) in 97% yield. It is toward these discoveries and the unexpected results obtained therefrom that the present disclosure is directed.

BRIEF SUMMARY OF THE INVENTION

A structure-activity relationship (SAR) study of the South African willow tree (*Combretum caffrum*) antineoplastic constituent combretastatin A-4 (3b) led to the discovery of a potent cancer cell growth inhibitor designated phenstatin (5a). This benzophenone derivative of combretastatin A-4 showed great antineoplastic activity and the benzophenone derivative of combretastatin A-1 was likewise synthesized. This, benzophenone, designated "hydroxyphenstatin" (6a), was synthesized by coupling of a protected bromobenzene and a benzaldehyde to give the benzhydrol with subsequent oxidation to the ketone. Hydroxyphenstatin was converted to the sodium phosphate prodrug (6e) by a dibenzyl phosphite phosphorylation and subsequent benzyl cleavage (6a→6d→6e). Hydroxyphenstatin (6a) was found to be a potent inhibitor of tubulin polymerization comparable to combretastatin A-1 (3a).

A principal object of the present invention is the synthesis, elucidation of structure and utilization of a novel antineoplastic compound obtained while attempting to synthesize anticancer substances related to combretastatin A-1, obtained from the South African willow tree (*Combretum caffrum*) and found to obtain greater potency, enhanced solubility and less adverse side effects than had been previously obtained from other compounds previously derived therefrom.

Another object of the present invention is the isolation, elucidation and utilization of a synthetic derivative of the potent cell growth inhibitor designated "phenstatin" in a continuing effort to develop synthetic agents capable of inhibiting the spread of cancer cells in the human environment with minimal side effects.

These and still further objects as shall hereinafter appear are readily fulfilled by the present invention in a remarkably unexpected manner as will be readily discerned from the following detailed description of an exemplary embodiment thereof.

BRIEF DESCRIPTION OF DRAWING

In the drawing:

FIG. 1 is a crystal structure of hydroxyphenstatin (6a) showing intermolecular H-bonding between the carbonyl oxygen O7 and the hydroxyl hydrogen or O10.

DESCRIPTION OF THE PREFERRED EMBODIMENT

As indicated above, the present invention relates generally to the field of chemotherapy and more particularly to the synthesis of novel anti-neoplastic agents denominated "hydroxyphenstatin" and selected prodrugs thereof which were discovered while attempting to synthesize compounds related to those obtained from the South African willow tree *combretum caffrum*. To enhance the of the following detailed description, reference is made to the statistical definitions and structural representations shown below, as Chart 1, which have been coded to correspond to the various references in this text and to illustrate the scheme defined herein and identified as Scheme 1 and Scheme 2.

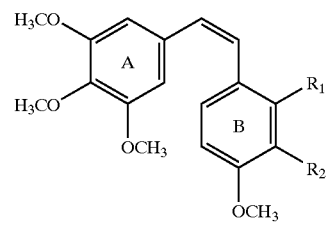

3a, R₁R₂ = OH
   Combretastatian A-1
b, R₁ = H, R₂ = OH
   Combretastatian A-4
c, R₁ = H, R₂ = OP(O)(ONa)₂
   Combretastatian A-4 prodrug
d, R₁ = H, R₂ = OSi(CH₃)₂C(CH₃)₃,
e, R₁R₂ = OP(O)(ONa)₂

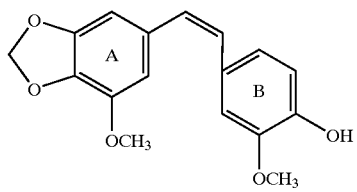

4, Combretastatin A-2

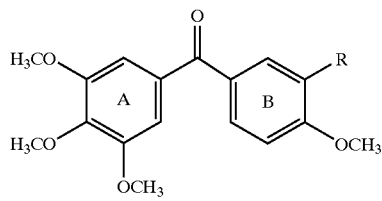

5a, R = OH, Phenstatin
b, R = OSi(CH₃)₂C(CH₃)₃

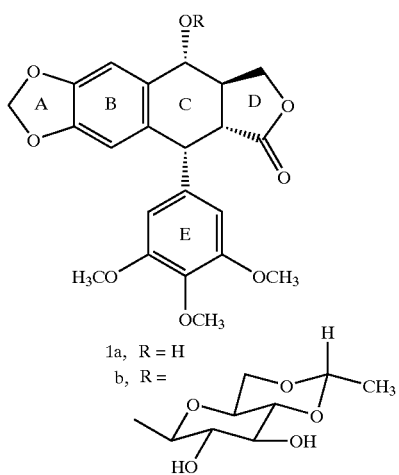

1a, R = H
b, R = [sugar group]

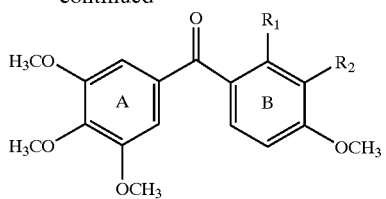

6a, R₁,R₂ = OH, Hydroxyphenstatin
b, R₁,R₂ = OTBDMS
c, R₁,R₂ = OCH₂OCH₃
d, R₁,R₂ = OP(O)OCH₂C₆H₅)₂
e, R₁,R₂ = OP(O)(ONa)₂

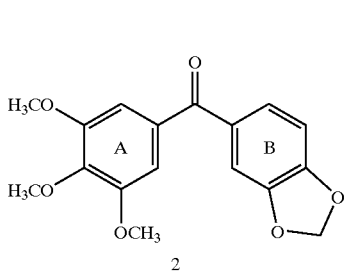

2

Scheme 1

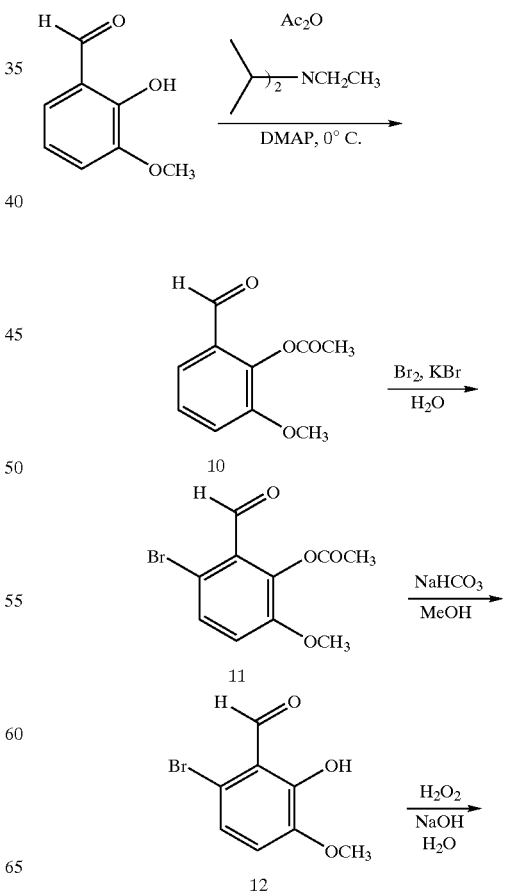

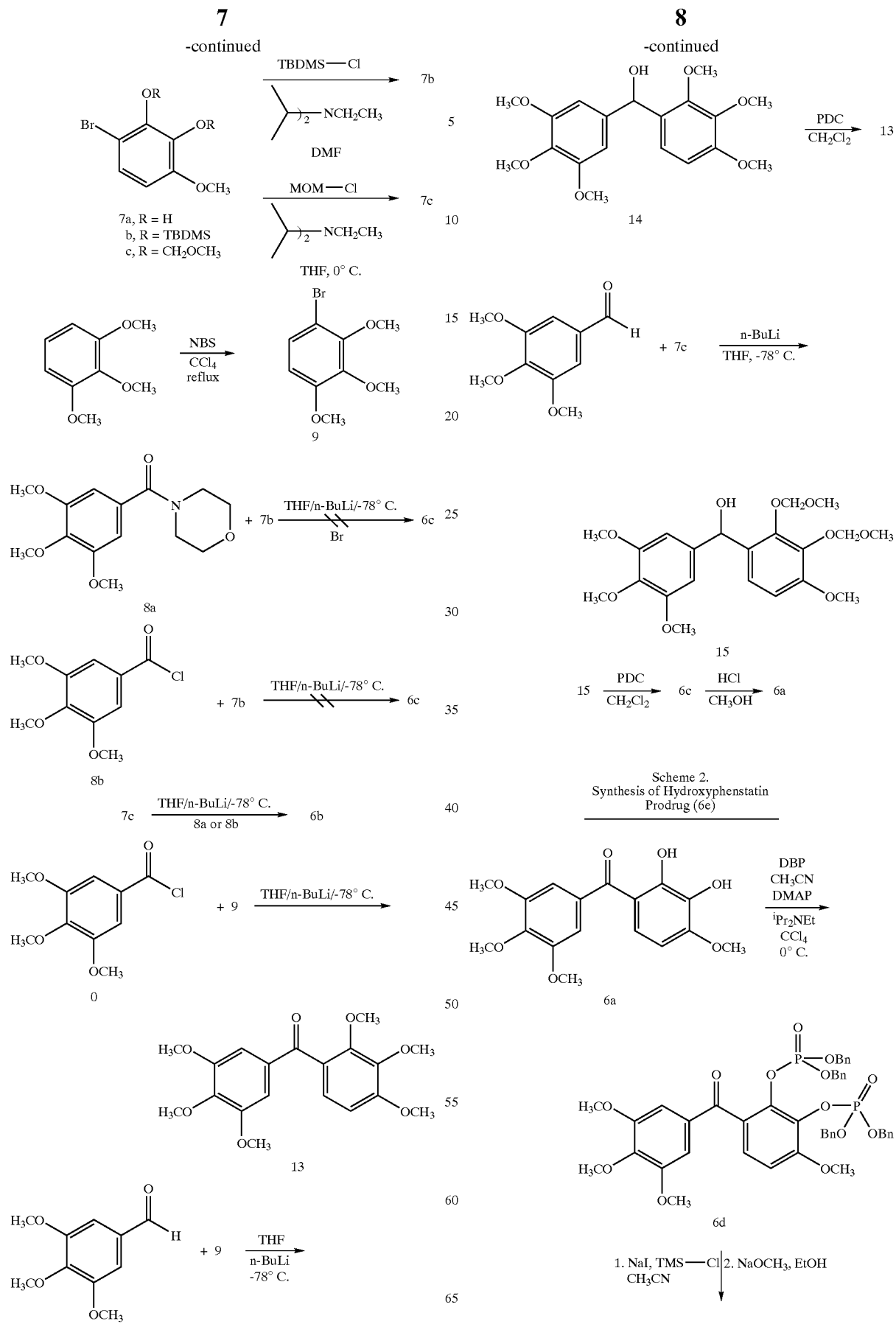

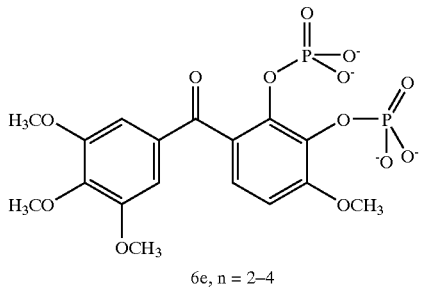

6e, n = 2–4

Statistical Definitions

The following measures are used to express drug activity giving the drug dose, which reduces cell growth to a specified percentage of growth:

$ED_{50}$ (P388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage.

TGI, (Total Growth Inhibition), is the drug dose needed to yield zero percent growth, e.g., just as many cells at the end of the experiment as were present in the beginning. Whether just as many cells were killed as were produced (steady state), or no growth occurred (total inhibition), cannot be distinguished.

$LC_{50}$, (Lethal Concentration 50%), is the drug concentration which reduces growth to –50%, i.e., removes half of the cells originally present at the beginning of the experiment.

Each drug is tested at five (5) doses: 100-10-1-0.1-0.01 µg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields a growth value higher than 50%, then $ED_{50}$<(lowest dose). Similar calculations are performed for the TGI at 0% growth, and at –50% growth for the $LC_{50}$.

In addition, the crystal structure of hydroxyphenstatin (6a) is shown in FIG. 1 and the $GI_{50}$ values obtained using hydroxyphenstatin against selected cell lines are shown in Table 1, below.

The crystal structure of hydroxyphenstatin (6a), as shown on FIG. 1, was established via single-crystal X-ray crystallography. The unit cell contained 4 molecules of the parent compound; each asymmetric unit consisting of two independent molecules of hydroxyphenstatin. In addition, adjacent molecules of hydroxyphenstatin are linked via intermolecular hydrogen bonding between the O10 carbonyl and O7 hydroxyl group.

Furthermore, the evaluation of hydroxyphenstatin (6a) the tetrasodium diphosphate prodrug (6e), against a series of Human Cancer Cells and Murine P388 Lymphocytic Leukemia and the $GI_{50}$ values obtained are shown in Table I, below.

TABLE I

Evaluation of Hydroxyphenstatin (6a), the Tetrasodium Diphosphate Prodrug (6e), Against a Series of Human Cancer Cell and Murine P388 Lymphocytic Leukemia.

| Cell Type | Cell Line | $GI_{50}$ µg/mL | | | |
|---|---|---|---|---|---|
| | | (6a) | (6c) | (6d) | (6e) |
| Leukemia | P388 | 0.315 | >10 | 2.55 | 0.0336 |
| Pancreas-a | BXPC-3 | 3.3 | >10 | >10 | 5.3 |
| Melanoma | RPMI-7951 | 0.58 | >10 | >10 | ND |
| CNS | SF-295 | 0.04 | >10 | >10 | 0.23 |
| Lung-NSC | NCI-H460 | 0.21 | >10 | >10 | 0.35 |
| Colon | KM20L2 | 1.2 | ND[a] | ND | 5.9 |
| Prostate | DU-145 | 0.048 | >10 | >10 | 0.3 |

[a]ND - No Data Available

In Table II, below, the interaction of hydroxyphenstatin (6a), its diphosphate derivative (6e), combretastatin A-1 (3a), combretastatin A-4 (3b) and its prodrug (3c) are shown.

Comparative testing of (6a) and (6e) in the NCI 60-cell screen revealed a differential cytotoxicity profile and potency (e.g., mean-panel $GI_{50}$ 1.67±0.24×10$^{-7}$ M) that were essentially indistinguishable from each other or from combretastatin A-4.

TABLE 2

Interactions with Tubulin of Hydroxyphenstatin (6a), its Diphosphate Derivative (6e), Combretastatin A-1 (3a), Combretastatin A-4 (3b) and its prodrug (3c)

| Compound Binding ± SD | Inhibition of Tubulin Polymerization (µM IC50 ± SD) | % Inhibition of Colchicine |
|---|---|---|
| 6a | 0.82 ± 0.2 | 77 ± 4 |
| 6e | >40 | ND[a] |
| 3a | 1.1 ± 0.07 | 99.6 ± 0.7 |
| 3b | 1.0 ± 0.05 | 98 ± 1 |
| 3c | >40 | ND |

[a]No Data Available

Hydroxyphenstatin (6a) was found to potently inhibit tubulin polymerization, and its activity appeared to be somewhat greater than that of combretastatin A-1 (3a) (Table 2). Nevertheless, 6a was somewhat less active than 3a as an inhibitor of the binding of [$^3$H]colchicine to tubulin (Table 2). The reason for the apparent difference in relative activities between the catalytic assembly assay and the stoichiometric colchicine binding assay is not understood. However, it has been observed with other colchicine site drugs, (See: Verdier-Pinard, P.; Lai, J-Y.; Yoo, H-D.; Yu, J.; Marquez, B.; Nagle, D. G.; Nambu, M.; White, J. D.; Falck, J. R; Gerwick, W. H.; Day, B. W.; Hamel, E. Structure-activity Analysis of the Interaction of Curacin A, the Potent Colchicine Site Antimitotic Agent, with Tubulin and Effects of Analogs on the Growth of MCF-7 Breast Cancer Cells. Mol. Pharmacol. 1998, 53, 62–76), and an analogous pattern was also observed when phenstatin (5a) and combretastatin A-4 (3b) were compared.

The antimicrobial activities of the *Combretum caffrum* constituents combretastatins A-1 and A-4 have been reported. (See: Pettit, G. R.; Lippert, J. W. III; Herald, D. L.; Pettit, R. K.; Hamel, E. Antineoplastic Agents 440. Asymmetric Synthesis and Evaluation of the Combretastatin A-1 SAR Probes (1S,2S) and (1R,2R)-1-2-Dihydroxy-1-(2',3'-dihydroxy-4'-methoxyphenyl)-2-(3",4",5"-trimethoxyphenyl)ethane. *J. Nat. Prod*, in preparation). While several precursors to the related compound sodium hydroxyphenstatin diphosphate (6e) exhibited antifungal and/or antibacterial action (Table III, supra), the prodrug (6e) did not. Compounds 6a, 6c, 7b, 8a, 13, 14, and 15 were also available in sufficient quantity for antibiotic screening. At 100 μg/disk, none of these compounds inhibited growth of the two fungal and eight bacterial strains tested.

Due to the greater improved therapeutic properties of the combretastatin A-4 sodium phosphate prodrug (3c) vs. the parent phenol (3b), the corresponding hydroxyphenstatin prodrug (6e) was synthesized (6a-e), (See: Scheme 2). The previous phosphorylation techniques was used for such syntheses, based on pentavalent and trivalent phosphorus precursors, were evaluated. They proved to be substantially less effective than employment of the dibenzyl phosphite approach. (See: Silverberg, L. J.; Dillon, J. L.; Vemishetti, P. A Simple, Rapid and Efficient Protocol for the Selective Phosphorylation of Phenols with Dibenzyl Phosphite. *Tetrahedron Lett.* 1996, 37, 771–774) The prodrug was synthesized in three steps from hydroxyphenstatin by phosphorylation of phenol (6a) utilizing dibenzyl phosphite (under basic conditions in acetonitrile), followed by cleavage of the benzyl groups (6d) with trimethylsilyl iodide (formed in situ) and reaction of the resulting phosphoric acid with sodium methoxide in ethanol to afford the sodium phosphate prodrug (6e) in 92% overall yield.

As expected, 6e was not active as an inhibitor of tubulin polymerization ($IC_{50}$>40 μM Table 2), as has been the case with other phosphorylated derivatives in the combretastatin series. However, its activity as an inhibitor of cancer cell growth (Table 1) was significant.

Experimental Section

All solvents were redistilled. Both the course and products from reactions were monitored by thin-layer chromatography using Analtech silica gel GHLF uniplates. Solvent extracts of aqueous solutions were dried over anhydrous sodium sulfate unless otherwise noted. Flash column chromatography was performed using silica gel (230–400 mesh ASTM).

Melting points were recorded employing an Electrothermal 9100 digital melting point apparatus and are uncorrected. The IR spectra were obtained using a Mattson FTIR model 2020 instrument. Low resolution mass spectral data were collected using a Varian MAT 312 instrument (EIMS). The high resolution FAB spectra were obtained at the Midwest Center for Mass Spectrometry employing a Kratos MS-50 mass spectrometer, University of Nebraska, Lincoln Nebr. All $^1$H— and $^{13}$C—NMR spectra determined using a Varian Gemini 300 MHZ instrument with $CDCl_3$ (TMS internal reference) as solvent unless otherwise noted. The $^{31}$P—NMR spectra were measured in $CDCl_3$ with 85% $H_3PO_4$ as an external standard employing a Varian Unity 500 MHZ instrument. The X-ray crystal structure data collection was performed on an Enraf-Nonius CAD4 diffractometer. Elemental analyses were determined by Galbraith Laboratories, Inc., Knoxville, Tenn.

2-Acetoxy-3methoxy-benzaldehyde (10).

To a solution of o-vanillin (10.1 g) and a catalytic quantity (0.8 g) of dimethylaminopyridine in N-diisopropylethyl amine (23 mL) at 0° C. was added acetic anhydride (8 mL). The solution was stirred overnight, poured into 2N hydrochloric acid (100 mL), extracted with dichloromethane and the solvent removed in vacuo to afford a yellow solid. Recrystallization from ethanol yielded yellow crystals (10.9 g, 85%): m.p. 75.4–76.2° C., lit[17] m.p. 76° C.; EIMS m/z 194 ($M^+$), 152, 106, 43.

2-Acetoxy-3methoxy-6bromo-benzaldehyde (11).

To a solution of potassium bromide (40 g) in $H_2O$ (250 mL) was added bromine (6.8 mL). To the dark red solution was added aldehyde 10 (20.2 g). The turbid orange solution was stirred overnight, filtered, rinsed with ethyl acetate, recrystallized from ethyl acetate/hexane to afford yellow crystals (22.4 g, 79%): m.p. 121.6–123.4° C., lit[18] m.p. 119–120° C.; EIMS m/z 274 ($M^+$, $^{81}$Br), 272 ($M^+$, $^{79}$Br), 232, 230, 186, 184, 43; $^1$H NMR δ 10.26 (1H, s, CHO), 7.51 (1H, d, J=9.0 Hz, $H_4$), 7.05 (1H, d, J=9.0 Hz $H_2$, $H_4$), 3.85 (3H, s, $OCH_3$), 2.38 (3H, s, $COCH_3$); $^{13}$C—NMR (75.5 MHZ) δ 190.38, 168.71, 151.78, 140.37, 131.41, 126.49, 117.69, 116.35, 56.40, 20.44. Anal. Calcd. For $C_{10}H_9O_4Br$: C, 43.98; H, 3.32. Found: C, 44.46; H, 3.55.

2-Hydroxy-3-methoxy-6bromo-benzaldehyde (12).

To the aldehyde 11 (17.7 g) in aqueous methanol (125 mL) was added sodium bicarbonate (7.6 g, 1.1 eq.) and the turbid bright yellow solution stirred for 2 hours. The solution was acidified, extracted with dichloromethane and the solvent removed in vacuo to afford a yellow solid. The product was recrystallized from ethyl acetate/hexane to afford yellow crystals (14.7 g, 98%): m.p. 105.6–106.4° C., lit[19] m.p. 102–103° C.; EIMS m/z 232 ($M^+$, $^{81}$Br), 230 ($M^+$, $^{79}$Br), 186, 107, 79, 54, 32; Anal. Calcd. For $C_8H_7O_3Br$: C, 41.59; H, 3.05. Found: C, 41.83; H, 3.27.

1-Bromo-2,3dihydroxy-4methoxy-benzene (7a).

Aldehyde 12 (23 g) was suspended in 2% sodium hydroxide (300 mL) and a solution of 30% hydrogen peroxide (15.8 g, 1.4 eq.) was added. After 2 hours, another portion of 30% hydrogen peroxide (1.4 eq.) was added and the solution stirred overnight. The reaction mixture was acidified, extracted with dichloromethane, washed with sodium thiosulfate and the solvent removed in vacuo to afford a tan solid. The solid was recrystallized from methanol to afford colorless crystals (14 g, 64%): m.p. 122.3–124.3° C., lit[20] m.p. 124–126° C.; EIMS m/z 220 ($M^+$, $^{81}$Br), 218 ($M^+$, $^{79}$Br), 205, 203, 177, 175, 95; $^1$HNMR δ 6.99 (1H, d, J=9.0 Hz, $H_5$), 6.42 (1H, d, J=9.0 Hz, $H_4$), 5.56 (1H, s, OH), 5.51 (1H, s, OH), 3.88 (3H, s, $OCH_3$); $^{13}$C—NMR (75.5 MHZ) δ 146.59, 140.95, 133.47, 122.21, 104.35, 101.55, 56.31; Anal. Calcd. For $C_7H_7O_3Br$: C, 38.39; H, 3.22. Found: C, 38.47; H, 3.36.

1-Bromo-2,3-bis(tert-butyldimethylsilyl-oxy)-4-methoxy-benzene (7b).

To a solution of diphenol 7a (0.51 g) in dry dimethylformamide (10 mL) was added successively diisopropylethylamine (1.25 mL, 3.1 eq.) and t-butyldimethylsilyl chloride (0.78 g, 2.2 eq.) and the mixture was stirred at room temperature under argon for 3 hours, (HCl evolution was noted). The reaction was terminated by adding ice. After extraction with dichloromethane, the combined solvent was washed with water, saturated sodium bicarbonate and water, and dried. Removal of solvent gave an oil which solidified on trituration with ether. The solid was recrystallized from methanol and afforded colorless crystals (0.92 g, 90%): m.p. 68.9–69.6° C.; EIMS m/z 448 ($M^+$, $^{81}$Br), 446 ($M^+$, $^{79}$Br), 443, 431, 391, 389, 167; IR (KBr, $cm^{-1}$) $v_{max}$ 2934, 2859, 1576, 1472, 1254, 1092, 845, 671; $^1$H NMR δ 7.06 (1, d, J=8.7 Hz, $H_6$), 6.42 (1H, d, J=8.7 Hz, $H_5$), 3.75 (3H, s, $OCH_3$), 1.06 (9H, s, $C(CH_3)$), 0.99 (9H s, $C(CH_3)$, 0.19 (6H, s, Si—$CH_3$×2); $^{13}$C NMR 75.5 MHZ) δ 151.74, 145.32, 138.06, 124.33, 108.36, 105.64, 55.04, 26.46, 26.12, 18.75, 18.73, –3.10, –3.85. Anal. Calcd. For $C_{19}H_{29}BrO_3Si_2$: C, 50.99; H, 7.88. Found: C, 51.00; H, 7.84.

1-Bromo-2,3-bis(methoxymethyloxy)-4-methoxy-benzene (7c).

To a solution of 1-bromo-2,3-dihydroxy-4-methoxy-benzene (5.0 g) and anhydrous tetrahydrofuran (20 mL) at 0° C. under argon was added diisopropylethylamine (8.0 mL). The solution was stirred for 15 min, methyloxymethyl chloride (3.5 mL) was added, and the reaction mixture stirred for 3 hours. The solution was poured into water (250 mL), extracted with dichloromethane and the solvent removed in vacuo to provide an orange oil. The oil was purified by flash column chromatography (hexane-ethyl acetate, 2:1) to yield a clear oil (6.4 g, 91%): EIMS m/z 308 ($M^+$, $^{81}Br$), 306 ($M^+$, $^{79}Br$), 232, 230, 45; IR (neat, $cm^{-1}$) $v_{max}$ 2963, 2836, 1221, 1159, 1084, 966; $^1H$ NMR δ 7.25 (1H, d, J=9.0 Hz, $H_5$), 6.61 (1H, d, J=9.0 Hz, $H_4$), 5.20 (2H, s, $OCH_2$), 5.13 (2H, s, $OCH_2$), 3.84 (3H, s, $OCH_3$), 3.66 (3H, s, $OCH_3$), 3.59 (3H, s, $OCH_3$); $^{13}C$—NMR (75.5 MHZ) δ 153.31, 148.24, 140.05, 127.49, 108.94, 108.73, 99.39, 98.73, 58.14, 57.46, 56.11. Anal. Calcd. For $C_{11}H_{15}O_5Br$: C, 43.02; H, 4.92. Found: C, 42.86; H, 4.93.

N-(3,4,5Trimethoxybenzoyl)-morpholine (8a)

Morpholine (0.8 mL) was slowly added to a solution composed of toluene (10 mL) and 3,4,5-trimethoxybenzoyl chloride (1.1 g). The reaction was accompanied by evolution of heat and precipitation of morpholine hydrochloride. After 3 hours, the solution was filtered and concentrated in vacuo to afford a white solid which was recrystallized from ethanol to afford colorless needles (1.2 g, 86%): m.p. 119.8–120.7° C., lit[3c] m.p. 120–121° C.; EIMS m/z 281 ($M^+$), 266, 195; $^1H$ NMR δ 6.63 (2H, s, $H_{2,6}$), 3.87 (6H, s, $OCH_3×2$), 3.86 (3H, s, $OCH_3$), 3.70 (8H, bs, $CH_2×4$).

1-Bromo-2,3,4-trimethoxy-benzene (9)

Pyrogallol trimethyl ether (5.1 g) was suspended in $CCl_4$ (60 mL) and N-bromosuccinimide (6.5 g, 1.2 eq.) was added. The reaction mixture was heated at reflux for 20 hours. The succinimide was collected and the filtrate concentrated in vacuo to a brown oil. The oil was separated by gravity column chromatography (hexane-ethyl acetate, 19:1) and yielded the title compound as a yellow oil (5.9 g, 78%): EIMS m/z 234 (($M^+$ —$CH_3$, $^{81}Br$), 232 ($M^+$ —$CH_3$, $^{79}Br$), 107, 95, 69, 58, 44; $^1H$ NMR ($CDCl_3$, 300 MHZ) δ 7.21 (1H, d, J=9.0 Hz, $H_6$), 6.58 (1H, d, J=9.0 Hz, $H_5$), 3.91 (3H, s, $OCH_3$), 3.89 (3H, s, $OCH_3$), 3.85 (3H, s, $OCH_3$).

2',3,3',4,4',5-Hexamethoxybenzophenone (13).

To a solution of bromobenzene 9 (0.21 g) in dry tetrahydrofuran (5 mL) cooled to −78° C. was added n-butyl lithium (0.38 mL, 2.5 M, 1.1 eq.). The solution was stirred for 30 min. and 3,4,5-trimethoxybenzoyl chloride (0.2 g) in anhydrous tetrahydrofuran was added. The resulting solution was then stirred for an additional 28 hours. The reaction was stopped with water, extracted with ethyl acetate and the solvent removed (in vacuo) to give a yellow oil. Separation by flash column chromatography (hexane-ethyl acetate, 3:1) afforded a colorless solid (0.06 g, 20.5%). The solid was recrystallized twice from ethyl acetate-hexane: m.p. 124.6–125.9° C., lit[22] m.p. 121° C.; EIMS m/z 362 ($M^+$), 345, 317, 181, 169, 151; $^1H$ NMR δ 7.11 (1H, d, J=9.0 Hz, $H_6$), 7.08 (2H, s, $H_{2,6}$), 6.72 (1H, d, J=9.0 Hz, $H_5$), 3.94 (3H, s, $OCH_3$), 3.93 (3H, s, $OCH_3$), 3.90 (3H, s, $OCH_3$), 3.85 (6H, s, $OCH_{3,3,5}$), 3.80 (3H, s, $OCH_3$).

2',3,3',4,4',5Hexamethoxydiphenylcarbinol (14).

The preceding experiment was repeated using bromobenzene 9 (0.55 g) anhydrous tetrahydrofuran (15 mL) and n-butyllithium (0.93 mL, 2.5 M, 1.05 eq.). A solution of 3,4,5-trimethoxybenzaldehyde (0.44 g) was added and the solution stirred for 16 hours. The resulting oily product was separated by flash column chromatography (hexane-ethyl acetate, 9:1) to give a clear oil (0.38 g, 47%): EIMS m/z 364 ($M^+$), 331, 315, 195, 181, 169; IR (neat, $cm^{-1}$) $v_{max}$ 3462, 2940, 2837, 1593, 1464, 1234, 1127, 1015; $^1H$ NMR δ 6.90 (1H, d, J=8.7 Hz, $H_6$), 6.64 (1H, d, J=8.7 Hz, $H_5$), 6.61 (2H s, $H_{2,6}$), 5.88 (1H, d, J=3.9 Hz, CH), 3.86 (3H, s, $OCH_3$), 3.85 (3H, s, $OCH_3$), 3.83 (3H, s, $OCH_3$), 3.82 (6H, s, $OCH_3×2$), 3.76 (3H, s, $OCH_3$); $^{13}C$ NMR (75.5 MHz) δ 153.37, 152.98, 151.20, 142.03, 139.55, 136.91, 129.63, 122.15, 106.98, 103.46, 72.03, 60.85, 60.74, 60.61, 56.01, 55.88. Anal. Calcd. For $C_{19}H_{23}O_7$; C, 62.63; H, 6.64. Found: C, 62.25; H, 6.97.

2',3'-Bis(methoxymethyloxy)-3,4,4',5tetramethoxydiphenylcarbinol (15).

To a solution of protected bromobenzene 7c (0.91 g, 2.95 mmol) in anhydrous tetrahydrofuran (5.0 mL) cooled to −78° C., n-butyl lithium (1.21 mL, 2.44 M, 2.95 mmol.) was added. The solution was stirred for 1 hour and 3,4,5-triethoxybenzaldehyde (0.58 g, 2.95 mmol) was added. The resulting solution was then stirred for an additional 4 hours. The reaction was ended by adding water and the mixture was extracted with ethyl acetate. Removal of solvent (in vacuo) led to a yellow oil that was separated by flash column chromatography (hexane-ethyl acetate, 9:1) to afford a clear oil that solidified upon standing (1.15 g, 92%). The solid was recrystallized from methanol and yielded colorless plates: m.p. 79.9–81.8° C.: HRMS 424.1749 $C_{21}H_{28}O_9$ EIMS m/z 424 ($M^+$), 362, 347, 331, 317, 289, 181; IR (KBr, $cm^{-1}$) $v_{max}$ 3407, 3001, 2942, 2836, 1236, 1155, 1123, 1063; $^1H$ NMR δ 6.71 (1H, d, J=9.0 Hz, $H_{6'}$), 6.68 (2H, s, $H_{2',6}$), 6.63 (1H, d, J=9.0 Hz, $H_5$), 6.09 (1H, d, J=3.3 Hz, CH), 5.20 (2H, dd, J=6.0, 10.5 Hz, $OCH_2$), 5.13 (2H, $OCH_2$), 3.85 (3H, s, $OCH_3$), 3.84 (6H, s, $OCH_3×2$), 3.82 (3H, s, $OCH_3$), 3.61 (3H, s, $OCH_3$), 3.58 (3H, S, $OCH_3$), $^{13}C$ NMR (75.5 MHz) δ 153.23, 153.05, 149.73, 138.17, 138.12, 136.80, 131.16, 123.52, 108.04, 104.32, 103.53, 100.03, 98.59, 69.79, 60.85, 57.74, 57.37, 56.07, 55.93. Anal. Calcd. For $C_{21}H_{27}O_9$: C, 59.43; H, 6.65. Found, C, 59.44; H, 6.82.

2',3'-Bis(methoxymethyloxy)-3,4,4',5-tetramethoxybenzophenone (6c).

To a stirred solution of diphenylcarbinol 15 (6.85 g) in dichloromethane (250 mL) was added 4 Å molecular sieves (9 g) and pyridinium dichromate (9.1 g, 1.5 eq.). The black solution was stirred overnight, filtered through Celite, rinsed with methanol and the solvent removed in vacuo to afford a black residue. The mixture was separated by flash column chromatography (hexane-ethyl acetate, 4:1) to provide a clear oil that solidified upon standing (6.5 g, 95%). The solid was recrystallized twice from ethyl acetate-hexane to afford colorless crystals: m.p. 70.2–71.7° C.; HRMS 422.1577 $C_{21}H_{26}O_9$; EIMS m/z 422 ($M^+$), 346, 195, 181; IR (KBr, $cm^{-1}$) $v_{max}$ 3005, 2944, 2845, 1649, 1583, 1231, 1125, 1071; $^1H$ NMR δ 7.16 (1H, d, J=8.5 Hz, $H_6$), 7.12 (2H, s, $H_{2,6}$), 6.78 (1H, d, J=8.5 Hz, $H_5$), 5.18 (2H, s, $OCH_22'$), 5.01 (2H, s, $OCH_2$), 3.93 (3H, s, $OCH_3$), 3.92 (3H, s, $OCH_3$), 3.85 (6H, s, $OCH_{3\ 3,5}$), 3.62 (3H, s, $OCH_3$), 3.26 (3H, s, $OCH_3$); $^{13}C$ NMR (75.5 MHz) δ 193.87, 155.93, 152.77, 149.48, 142.42, 138.80, 133.07, 127.35, 125.48, 107.64, 107.36, 99.76, 98.66, 60.92, 57.41, 57.32, 56.22, 56.05. Anal. Calcd. For $C_{21}H_{26}O_9$: C, 59.71; H, 6.20. Found: C, 59.75; H, 6.28.

Hydroxyphenstatin (2',3'-Dihydroxy-4-methoxy-phenyl)-3,4,5-trimethoxy-phenyl)-methanone (6a).

To a stirred solution of MOM-protected hydroxyphenstatin 6c (0.120 g, 0.284 mmol) in methanol (10.0 mL) was added 1 N HCl (0.57 mL) and the solution stirred for 2 hours. The reaction mixture was poured into water, extracted with dichloromethane and the solvent evaporated in vacuo to yield a yellow solid (0.09 g, 99%). The solid was recrystallized (twice) from methanol: m.p. 171.1–171.9° C.; HRMS 334.1052 $C_{17}H_{17}O_7$; EIMS m/z 334 ($M^+$), 303, 195, 168, 153; IR(KBr, $cm^{-1}$) $v_{max}$ 3273, 3100, 3001, 2944, 1636, 1574, 1121, 1063; $^1H$ NMR δ 12.23 (1H, s, OH), 7.27 (1H, d, J=8.7 Hz, $H_6$), 10 6.92 (2H, s, $H_{2,6}$), 6.51 (1H, d, J=8.7 Hz, $H_5$), 5.57 (1H, s, OH), 3.99 (3H, s, $OCH_3$), 3.94 (3H, s, $OCH_3$), 3.90 (6H, s, $OCH_3×2$); $^{13}C$ NMR (75.5

MHz) δ 199.58, 152.93, 152.08, 150.94, 141.33, 133.67, 133.13, 125.59, 113.99, 106.80, 102.53, 60.98, 56.32, 56.24. Anal. Calcd. For $C_{17}H_{18}O_7$: C, 61.07; H, 5.43. Found: C, 61.07; H, 5.37.

X-Ray Crystal Structure Determination of Hydroxyphenstatin (6a). A thick, plate-shaped X-ray sample (~0.38×0.36× 0.08 mm), grown from methanol solution, was mounted on the tip of a glass fiber with Super-Glue. Data collection was performed at 301±1° K. Accurate cell dimensions were determined by least-squares fitting of 25 carefully centered reflections in the range of 35°<è<40° using Cu Ká radiation. 2',3'-O-Di-(bisbenzylphosphoryl)-hydroxyphenstatin (6d).

To a solution of hydroxyphenstatin 6a (4 g) in dry acetonitrile (100 mL) and carbon tetrachloride (11.4 mL, 10 eq.) was added dimethylaminopyridine (0.14 g, 0.1 eq.) and diisopropylethylamine (8.7 mL, 4.2 eq.). After cooling to −10° C., dibenzylphosphite (7.8 mL, 3.0 eq.) was added and the solution stirred for 16 hours under argon at −10° C. and then brought to room temperature. The reaction was terminated with 0.5 M $KH_2PO_4$, extracted with ethyl acetate and the combined solvent was washed with brine and dried. Removal of solvent (in vacuo) afforded an orange oil which was separated by flash column chromatography (hexane-ethyl acetate, 1:1 to 0:1) to provide a white solid (9.7 g, 96%). The solid was recrystallized twice from ethyl acetate-hexane: m.p. 86.9–87.4° C.; EIMS m/z 854 ($M^+$), 656, 576, 514, 486, 91; IR (KBr, $cm^-$) $v_{max}$ 2967, 2945, 2841, 1659, 1298, 1020, 951; $^1H$ NMR δ 7.44 (1H, d, J=9.0 Hz, $H_{6'}$), 7.27 (18H, m, Ar—H), 7.11 (2H, s, $H_{2,6}$), 7.08 (2H, m, Ar—H), 6.92 (1H, d, J=9.0 Hz, $H_{5'}$), 5.23 (2H, s, $CH_2Bn$), 5.21 (2H, s, $CH_2Bn$), 4.64 (2H, dd, J=4.5, 6.9 Hz, $CH_2Bn$), 4.77 (2H, dd, J=4.5, 6.9 Hz, $CH_2Bn$), 3.84 (3H, s, $OCH_3$), 3.80 (6H, s, $OCH_{3\,3,5}$), 3.77 (3H, s, $OCH_3$); $^{13}C$ NMR (75.5 MHZ) δ 191.73, 171.11, 154.84, 152.84, 142.20, 135.81, 135.74, 135.24, 135.18, 132.77, 128.42, 128.37, 128.29, 127.96, 127.67, 127.58, 125.90, 109.19, 107.55, 69.98, 69.93, 69.87, 69.82, 60.80, 60.36, 56.30, 56.23; $^{31}P$ NMR (DMSO, decoupled, −202.35 MHZ) δ −5.01, −5.79. Anal. Calcd. For $C_{45}H_{44}O_{13}P_2$: C, 63.23; H, 5.19. Found: C, 62.81; H, 5.58.

Sodium Hydroxyphenstatin Diphosphate (6e)

A mixture of the phosphorylated hydroxyphenstatin (6d) (9.0 g) and sodium iodide (6.3 g, 4.0 eq.) in anhydrous acetonitrile (30 mL) was stirred (under argon) and trimethylsilyl chloride (5.4 mL, 4.0 eq.) was added. The solution was stirred for 2 hours and the reaction was stopped with water. After extraction with ethyl acetate, the aqueous layer was concentrated to a light brown foam. To the residue in ethanol (75 mL) was added sodium methoxide (2.3 g, 4.0 eq.) and the solution stirred for 12 hours. The reaction mixture was concentrated and the residue crystallized from water-acetone to yield an amphorous solid (5.6 g, 92%) which was recrystallized (three times) from water-acetone: m.p. 145.7–147.2; LRFAB m/z 583.1 ($M+H^+$), calcd. 583.2; IR (KBr, $cm^{-1}$) $v_{max}$ 3009, 2947, 2843, 1643, 1343, 1289, 1182, 1123, 990; $^1H$ NMR ($D_2O$, 500 MHZ) δ 7.07 (2H, s, $H_{2,6}$), 6.98 (1H, d, J=5.1 Hz, $H_{6'}$), 6.75 (1H, d, J=5.1 Hz, $H_{5'}$), 3.80 (3H, s, $OCH_3$), 3.75 (6H, s, $OCH_3×2$), 3.74 (3H, s, $OCH_3$); $^{13}C$ NMR ($D_2O$, reference to $CDCl_3$, 75.5 MHZ) δ 197.15, 156.15, 152.24, 145.03, 141.38, 135.70, 133.99, 126.37, 125.49, 108.72, 106.95, 61.16, 56.40, 56.30; $^{31}P$ NMR ($D_2O$, decoupled, −202.35 MHZ) δ 0.05, −1.49. The solubility of sodium hydroxyphenstatin diphosphate was found to be 100 mg/mL in distilled water at 25° C.

Lithium Hydroxyphenstatin Diphosphate (6f)

To the light brown foam in methanol (10 mL) was added lithium hydroxide (0.049 g, 4.0 eq.) and the solution stirred for 12 hours. The reaction mixture was concentrated and the residue crystallize from water-acetone to yield an amphorous solid (0.11 g, 74%) which was recrystallized from water-acetone: m.p. 174–176° C. (dec.); LRFAB m/z 511 ($M^+$), 505 ($M^+$-Li), 499 ($M^+$-2Li), 493 ($M^+$-3Li), 435, 413, 199; IR (KBr, $cm^{-1}$) $v_{max}$ 3011, 2945, 2845, 1632, 1339, 1283, 1187, 1127, 1003; $^1H$ NMR ($D_2O$, 300 MHz) δ 7.13 (2H, s, $H_{2,6}$), 6.96 (1H, d, J=7.5 Hz, $H_{6'}$), 6.69 (1H, d, J=7.5 Hz, $H_{5'}$), 3.77 (6H, s, $OCH_3×2$), 3.76 (3H, s, $OCH_3$), 3.75 (3H, s, $OCH_3$); The solubility of lithium hydroxyphenstatin diphosphate was found to be 25 mg/mL in distilled water at 25° C.

Potassium Hydroxyphenstatin Diphosphate (6 g)

To the light brown foam in methanol (10 mL) was added potassium hydroxide (0.065 g, 4.0 eq.) in water (5 mL) and the solution stirred for 12 hours. The reaction mixture was concentrated and the yellow solid crystallized from water-acetone to yield an amphorous solid (0.161 g, 86%) which was recrystallized from water-acetone: m.p. 141–143° C. (dec.); LRFAB m/z 647 ($M^+$-K), 545, 395, 333, 181; IR (KBr, $cm^{-1}$) $v_{max}$ 3010, 2946, 2843, 1640, 1335, 1269, 1169, 1123, 988; $^1H$ NMR ($D_2O$, 300 MHz) δ 7.14 (2H, s, $H_{2,6}$), 6.96 (1H, d, J=8.1 Hz, $H_{6'}$), 6.69 (1H, d,8.1 Hz, $H_{5'}$), 3.77 (6H, s, $OCH_3×2$), 3.76 (3H, s, $OCH_3$), 3.75 (3H, s, $OCH_3$); The solubility of potassium hydroxyphenstatin diphosphate was found to be >100 mg/mL in distilled water at 25° C.

Calcium Hydroyphenstatin Diphosphate (6 h)

To the light brown foam in methanol (10 mL) was added calcium acetate (0.102 g, 2.0 eq.) and the solution stirred for 12 hours. The reaction mixture was concentrated and the residue crystallized from water-acetone to yield an amphorous solid (0.159 g, 79%) which was recrystallized from water-acetone: m.p. 186–188° C. (dec.); LRFAB m/z 531 ($M^+$), 493, 413, 395, 277; IR (KBr, $cm^{-1}$) $v_{max}$ 3011, 2940, 2847, 1638, 1337, 1296, 1182, 1127, 964; $^1H$ NMR ($D_2O$, 300 MHz) δ 7.13 (1H, d, J=8.4 Hz, $H_{6'}$), 7.07 (2H, s, $H_{2,6}$), 6.84 (1H, d, J=8.4 Hz, $H_{5'}$), 3.82 (3H, s, $OCH_3$), 3.76 (6H, s, $OCH_3×2$), 3.75 (3H, s, $OCH_3$); The solubility of calcium hydroxyphenstatin diphosphate was found to be <1 mg/mL in distilled water at 25° C.

Antimicrobial Susceptibility Testing

The new substances were screened against the bacteria *Stenotrophomonas maltophilia, Micrococcus luteus, Staphylococcus aureus, Escherichia coli, Enterobacter cloacae, Enterococcus faecalis, Streptococcus pneumoniae, Neisseria gonorrhoeae*, and the fungi *Candida albicans* and *Cryptococcus neoformans*, according to established disk susceptibility testing protocols. The results of these screens are shown in Table 1, below.

TABLE III

Antimicrobial activities of sodium hydroxyphenstatin phosphate precursors.

| Compound | Microbe(s) inhibited | Minimum inhibitory Concentration (μg/disk) |
|---|---|---|
| 6d | *Micrococcus luteus* | 50–100 |
| 10 | *Cryptococcus neoformans* | 25–50 |
|  | *Stenotrophomonas maltophilia* | 50–100 |
| 11 | *C. neoformans* | 6.25–12.5 |
|  | *Candida albicans* | 12.5–25 |
|  | *Escherichia coli* | 50–100 |
|  | *Neisseria gonorrhoeae* | 25–50 |
| 12 | *C. neoformans* | 12.5–25 |
|  | *C. albicans* | 50–100 |
|  | *N. gonorrhoeae* | 12.5–25 |

TABLE III-continued

Antimicrobial activities of sodium hydroxyphenstatin phosphate precursors.

| Compound | Microbe(s) inhibited | Minimum inhibitory Concentration (µg/disk) |
|---|---|---|
| 7a | S. maltophilia | 25–50 |
|  | E. coli | 50–100 |
|  | Staphylococcus aureus | 25–50 |
|  | N. gonorrhoeae | <6.25 |

*at 100 µg/disk, no inhibition of the ten bacteria and fungi tested

Tubulin Assays

The tubulin polymerization and colchicine binding assays were performed as described previously (See: Cardellicchio, C.; Fiandanese, V.; Marchese, G.; Ronzini, L. Functionalized Ketones by Iron Mediated Reaction of Grignard Reagents with Acyl Chlorides. *Tetrahedron Lett.* 1987, 28, 2053–2056), except that Beckman DU7400/7500 spectrophotometers equipped with "high performance" temperature controllers were used in the former assay. Unlike the manual control possible with the previously used Gilford spectrophotometers, the polymerization assays required use of programs provided by MDB analytical Associates, South Plainfield, N.J., since the Beckman instruments are microprocessor controlled. The Beckman instruments were unable to maintain 0° C., and the lower temperature in the assays fluctuated between 2 and 4° C. Temperature changes were, however, more rapid than in the Gilford instruments with the jump from the lower temperature to 30° C. taking about 20 sec. and the reverse jump about 100 sec.

FIG. 1. Crystal structure of hydroxyphenstatin (6a), showing intermolecular H-bonding between the carbonyl oxygen O7 and the hydroxyl hydrogenon O 10.

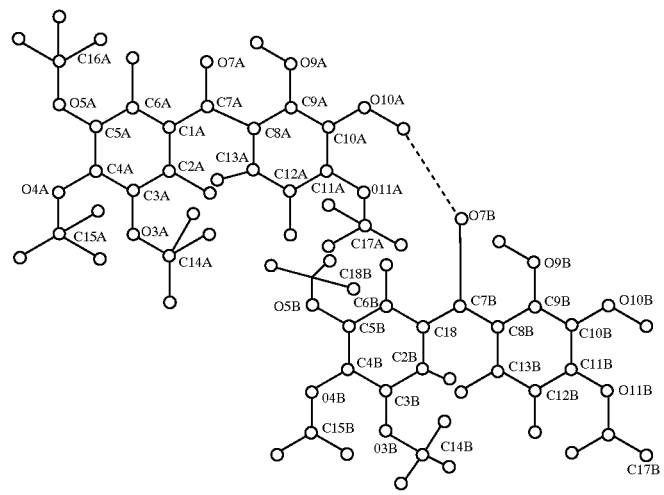

Dosing.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration on such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the imitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing and other forms as herein described.

The active ingredients to be employed as antineoplastic agents can be easily prepared in such unit dosage form with the employment of pharmaceutical materials which themselves are available in the art and can be prepared by established pores. The following preparations are illusive of the preparation of the unit dosage forms of the present invention, and not as a limitation thereof. Several dosage forms were prepared embodying the present invention. They are shown in the following examples in which the notation "active ingredient" signifies either hydroxyphenstatin 3a and/or hydroxyphenstatin prodrug 3e, and/or benzophenones 6c, 13 or any other compound described herein.

COMPOSITION "A"

Hard-Gelatin Capsules

One thousand two-piece hard gelatin capsules for oral use, each capsule containing 200 mg of an active ingredient are prepared from the following types and amounts of ingredients:

| Active ingredient, micronized | 200 g |
|---|---|
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are used for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

COMPOSITION "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 200 mg of an active ingredient, are prepared from the following types and amounts of ingredients:

| | |
|---|---|
| Active ingredient, micronized | 200 g |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly nixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

COMPOSITION "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 20 mg of an active ingredient in each milliliter, is prepared from the following types and amounts of ingredients:

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

What is claimed is:

1. A compound denominated hydroxyphenstatin and having the structure shown below:

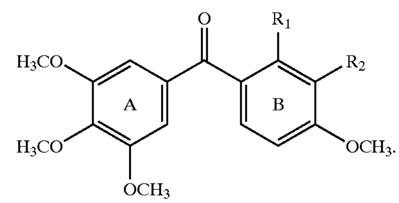

2. A compound for inhibiting the growth of cells afflicted with neoplastic disease comprising X-hydroxyphenstatin diphosphate wherein "X" is selected from the group consisting of sodium, lithium, potassium and calcium.

3. A method of treating cells afflicted with a neoplastic disease to inhibit the growth of said cells comprising: administering to said cells an effective amount of an active ingredient selected from the group consisting of hydroxyphenstatin and X-hydroxyphenstatin diphosphate wherein "X" is selected from sodium, calcium, lithium and potassium in a pharmaceutically acceptable carrier.

4. A method according to claim 3 in which said carrier comprises an aqueous solution.

* * * * *